United States Patent [19]
Vogt et al.

[11] Patent Number: 5,734,113
[45] Date of Patent: Mar. 31, 1998

[54] SURGICAL TORQUE WRENCH WITH A TORQUE INDICATOR

[75] Inventors: Martin Vogt, Waldenburg; Werner Schmutz, Niederdorf; Hans Schürch, Titterten; Eduardo Stadelmann, Lausanne, all of Switzerland

[73] Assignee: Institut Straumann AG, Waldenburg, Switzerland

[21] Appl. No.: 527,606

[22] Filed: Sep. 13, 1995

[30] Foreign Application Priority Data

Sep. 27, 1994 [CH] Switzerland ............... 2921/94

[51] Int. Cl.$^6$ ............................................. G01L 5/24
[52] U.S. Cl. .............................. 73/862.23; 73/862.21; 73/1.12; 81/467
[58] Field of Search ................ 73/862.21, 862.22, 73/862.23, 862.191, 1 C, 1.12; 81/467, 477, 478

[56] References Cited

U.S. PATENT DOCUMENTS

| | | | |
|---|---|---|---|
| 2,242,613 | 5/1941 | Mandl | 73/862.23 |
| 2,888,825 | 6/1959 | Krafft | 73/862.21 |
| 2,934,946 | 5/1960 | Engquist | 73/862.21 |
| 3,076,362 | 2/1963 | Able | 73/862.23 X |
| 3,274,827 | 9/1966 | Sturtevant | 73/862.23 |
| 3,386,284 | 6/1968 | Hejzlar | 73/862.08 |
| 3,391,573 | 7/1968 | Hiller | 73/862.22 |
| 3,587,307 | 6/1971 | Newberg . | |
| 3,664,186 | 5/1972 | Kraus | 73/862.23 |
| 3,703,827 | 11/1972 | Cole | 73/862.23 |
| 3,738,152 | 6/1973 | Green | 73/1 C X |
| 3,967,513 | 7/1976 | Myrdal | 73/862.23 X |
| 4,226,127 | 10/1980 | Hardiman | 73/862.23 X |
| 4,244,434 | 1/1981 | Wilson | 73/862.23 X |
| 4,488,442 | 12/1984 | Pacinelli | 72/862.21 |
| 4,805,464 | 2/1989 | Grabovac | 73/862.23 X |
| 4,977,775 | 12/1990 | Grabovac et al. | 73/1 C |
| 5,345,845 | 9/1994 | Myers . | |

FOREIGN PATENT DOCUMENTS

| | | |
|---|---|---|
| 0393852 | 10/1990 | European Pat. Off. . |
| 1498385 | 1/1968 | France . |

*Primary Examiner*—Elizabeth L. Dougherty
*Attorney, Agent, or Firm*—Anderson, Kill & Olick, P.C.

[57] ABSTRACT

The torque wrench (1) comprises a torque instrument (10) which is known per se—in the present case a ratchet instrument—as well as a torque indicator (40) which can be attached thereto. The torque indicator (40) possesses a sleeve-shaped support (41) which can be pushed onto the handle (12) of the torque instrument (10) and on which a linearly elastic bending rod (51) is fastened. Upon operation, the force (F) is exerted upon the free end of the bending rod (51) and the torque generated is displayed on a graduation (48). At its very front the support (41) possesses a non-rotationally symmetrical insertion zone (42) which receives the transition region (121) of the handle (12) in a manner fixed against rotation. The principal advantages of the torque wrench (1) are its dismantlability and the combination possibilities. The display accuracy of the torque indicator (40) is checked using a special test device.

7 Claims, 4 Drawing Sheets

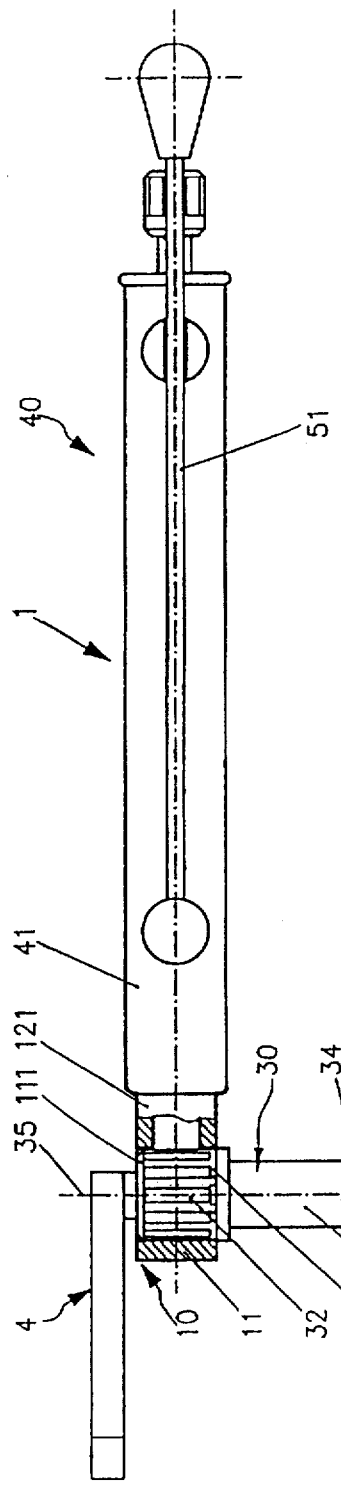
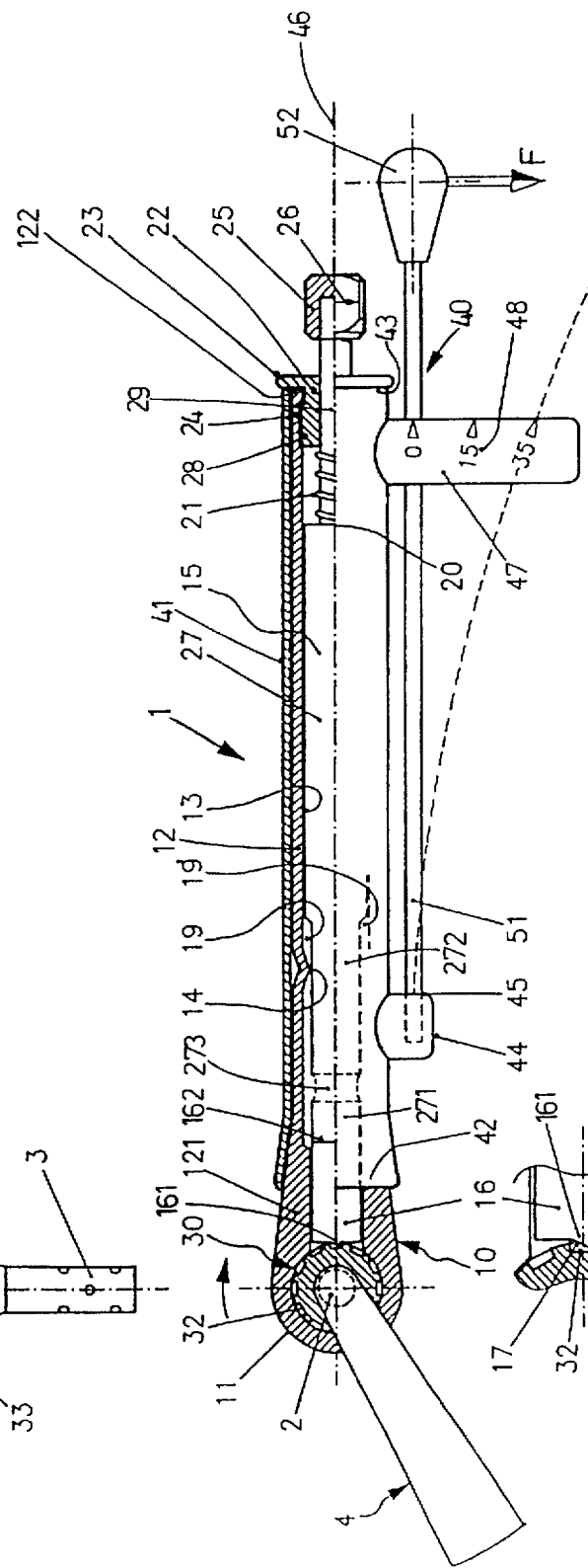

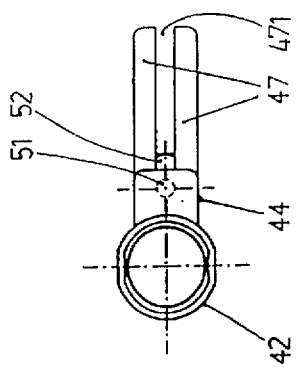
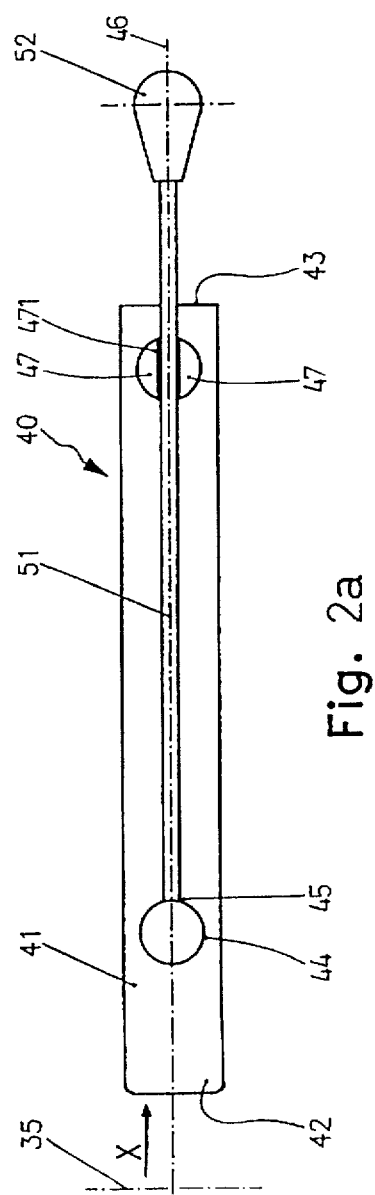
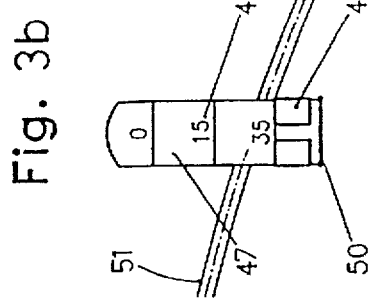
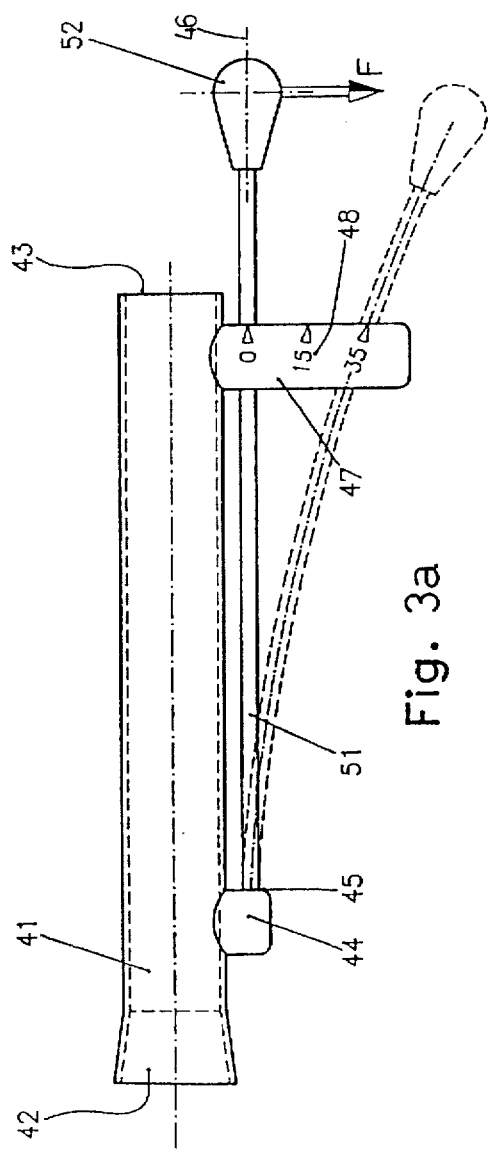

SURGICAL TORQUE WRENCH WITH A TORQUE INDICATOR

BACKGROUND OF THE INVENTION

1. Field of the invention

The invention relates to a torque wrench for use in surgery, which comprises a torque instrument known per se and a torque indicator attachable thereto as an accessory. Furthermore, the invention comprises a test device for control of the accuracy of display of torques exerted upon the torque wrench.

From dentistry, for example, it is known to insert implants (primary components) into the jaw bone and to fasten connection elements, namely special screws and superstructures, on the implants by screwing. Long-term stability and reliability of the screw connections essentially depend on the screw connections being carried out with the optimum torque in each case. Inadequate tightening, i.e. an excessively low torque, can subsequently lead to loosening of the screw connections. Excessive tightening, i.e. an excessively high torque, overloads the connection elements employed, increases the risk of fracture of the latter and jeopardizes the reliable anchorage of the implant in the bone.

2. Description of Prior Art

In their conventional design, surgical torque wrenches, e.g. in the form of a ratchet wrench, do not possess any additional torque indicator or a torque limiting mechanism (cf. Spiekermann, H.: Farbatlanten der Zahnmedizin (Odontological Coloured Atlases), vol. 10 Implantologie (Implantology). Georg Thieme Verlag, Stuttgart 1994, p. 53). Moreover, there are wrenches that are equipped with a mechanical or electronic torque limitation. Mechanical torque instruments are usually provided with a mechanism that possesses a pivotable lever or a rotatable catch on the ratchet head, so that the force of a pretensioned compression spring is overcome when the permissible torque is exceeded and the lever is thus bent or the catch comes out of engagement. A torque wrench having a slip clutch is disclosed in Spiekermann, loc.cit., page 33.

The torque instruments that have been conventional hitherto possess the disadvantage that only a relatively small range of the torque M is determined with a particular compression spring, e.g. with $M \leq 18$ Ncm. However, implantology requires torques of $M=30$ Ncm in some cases; in specific implant systems it is even necessary to have torques of $M=45$ Ncm and $M=60$ Ncm. If adjustability of the torque is dispensed with, an instrument with fixed settings must be available for each limited torque. This means that the user has to buy a fairly large range of instruments, which leads to increased expenditure. Moreover, the use of a compression spring for torque limitation is not ideal in any way. Use of a compression spring implies positive locking between a movable part (e.g., a pivoting arm) and a fixed part (e.g. a catch ball), it being necessary for frictional forces to be overcome because the pivotable arm has to slide over the ball transmitting the pressure force. However, the frictional relationships change quickly in an undetermined manner due to roughened surfaces, deposits, etc. The conventional torque instruments with torque limitation are very sensitive, and some of them possess components which can be cleaned only with excessive expenditure.

Due to the abovementioned interfering influences the accuracy and reproducibility of the torque limitation are adversely affected. Tests with conventional torque instruments revealed inaccuracies of ±10% in the range $20 \text{ Ncm} \leq M \leq 60$ Ncm. Admittedly, many torque instruments indicate if the envisaged torque is exceeded, e.g. by coming out of engagement, bending or emitting a noise, but exact adherence to the torque limitation is not ensured. Moreover, the increase in torque on tightening, e.g. of a screw, cannot be read off, i.e. monitored, with these instruments.

On electrical torque instruments it is usually possible to set various values of torque limitation and to read off the instantaneous torque value. Electrical instruments of this type are, however, many times more expensive than mechanical ones. In addition, fairly large inaccuracies may also occur frequently on electrical instruments. Thus, an error of ±10% in the range $0 \text{ Ncm} \leq M \leq 45$ Ncm was found in an instrument with slip coupling. Since these tolerances are hardly checkable by the user it is impossible to effect screw connections with the instruments in an optimum way. Thus, follow-up examinations of patients with dental prostheses supported by implants revealed loose screw connections which may endanger the entire reconstruction.

Accordingly, surgical torque instruments must permit precise, controlled operation. They must be designed such that a defined tension is imparted to a connection element, e.g. a screw, when it is screwed in. If a patient is to receive a more complex prosthesis with several screw connections, all screw connections will have to be carried out with the same tightening torque for uniform distribution of tension. For example, screw connections between a dental implant and a superstructure must not become loose spontaneously, and excessive tightening must not lead to fracture of screws or other structural elements or to bone damage.

Torque wrenches with a torque indicator are known from mechanical engineering. FR-A-1 498 385 describes a torque wrench having a basic member on which there is located a contoured carrier element, with two bending rods, running parallel to each other and having different moduli of elasticity, extending from the basic member. Deflection of the bending rod that is operated in each particular case is a measure of the torque exerted, which can be read off a scale. A first bending rod is firmly connected to the scale support, whereas the second bending rod projects through the groove in the scale support and is guided therein so as to be longitudinally displaceable. A scale allocated to the particular bending rod is applied on either side of the groove. If force is applied to the first bending rod the latter is bent and the scale support is pulled away together with it, as a result of which the second, unactuated bending rod engages in the groove and thereby displays the magnitude of the torque. If the force acts upon the second bending rod the latter is bent in the direction of the groove.

According to U.S. Pat. No. 3,587,307, a tensioning device for fixation of a ring spanner is provided on a torque indicator. A bending rod extends from the tensioning device, and a vertically aligned scale support and, finally, a handle are firmly provided on the other end of said bending rod. An indicator extends to the scale support from the tensioning device in parallel with the bending rod. The handle and the reception opening for the ring spanner oppose each other diametrically. The bending rod is bent on application of the ring spanner to a screw and on application of force upon the handle. The scale support is also deflected, whereas the indicator retains its position, so that deflection from the zero position can be read off as a measure of the torque exerted.

The abovementioned torque wrenches from mechanical engineering cannot be employed as surgical instruments purely by miniaturizing them.

In view of the structural and functional characteristics which distinguish the existing surgical torque wrenches and which must be judged critically, the invention is based on the following problem. A torque wrench is to be provided with a torque indicator, and the overall structure is to be composed of members that are as simple as possible and can be largely dismantled. Individual handling, increasing surface roughness, deposits or corrosion must not result in errors. It is desired to have a torque indicator which can be coupled with existing ratchet instruments. At the same time, the torques exerted must be controllable and reproducible. It should always be possible to read the varying torque value off a scale, e.g. in the range. 0 Ncm≦M≦40 Ncm. The responsibility for the maximum tightening torque exerted resides with the user, so that he can consider the recommended values of the supplier of the connection elements and his own empirical values depending on the individual situation. Finally, the geometrical dimensions and the shape of the complete torque wrench must permit unproblematical handling of the instrument at the various positions in the mouth of the patient. Proper display of the torque wrench is to be controlled with a test device at specific intervals.

SUMMARY OF THE INVENTION

The objects of the present invention are achieved by providing a surgical torque wrench including a torque instrument, a torque indicator formed as an elongated rigid support mountable on the torque instrument, a linearly elastic bending rod extending along the support and having one of its ends firmly secured at a clamping site provided on the support, and a graduation provided at the support end remote from the clamping site and extending transverse to the support for indicating a torque generated by application of a force to the free end of the bending rod which, causes the deflection of the bending rod relative to the graduation.

BRIEF DESCRIPTION OF THE DRAWINGS

An exemplary embodiment of the torque wrench with torque indicator, according to the invention, is described below in detail with reference to the attached drawings, possible modifications being mentioned finally. In the drawings:

FIG. 1a shows, in frontal view, a partial section with a torque wrench in the form of a ratchet instrument, screwing-in tool inserted therein and guide wrench attached to the very top thereof, as well as the torque indicator attached to the ratchet instrument;

FIG. 1b shows the plan view according to FIG. 1a;

FIG. 1c shows, as a detail, the engagement between the catch nose of the ratchet instrument and a groove in the screwing-in tool;

FIG. 2a shows the separate torque indicator in the view according to FIG. 1a;

FIG. 2b shows the side view according to FIG. 2a in arrow direction X;

FIG. 3a shows the separate torque indicator in the view according to FIG. 1b;

FIG. 3b shows the scale of the torque indicator with a maximum indicator;

DETAILED DESCRIPTION OF THE PREFERRED EMBODIMENTS

FIG. 1a

Figure 4A:
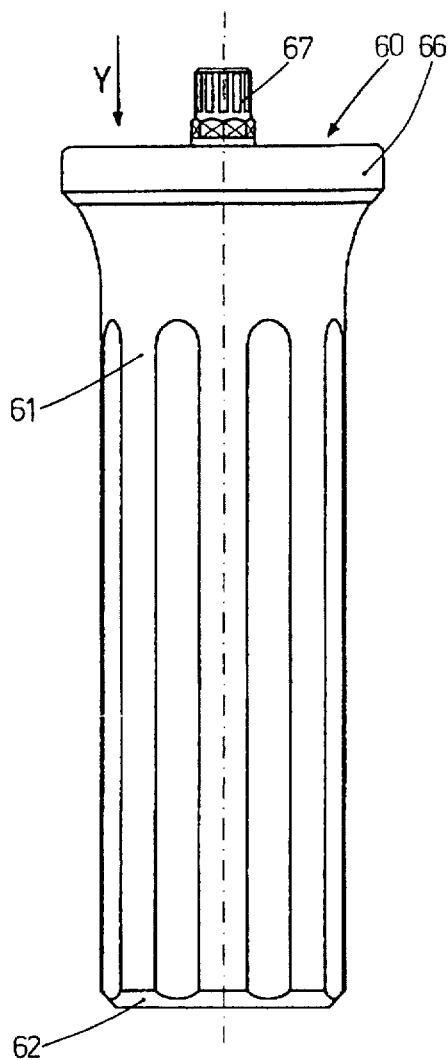
FIG. 4a shows the frontal view of the test device.
Figure 4B:
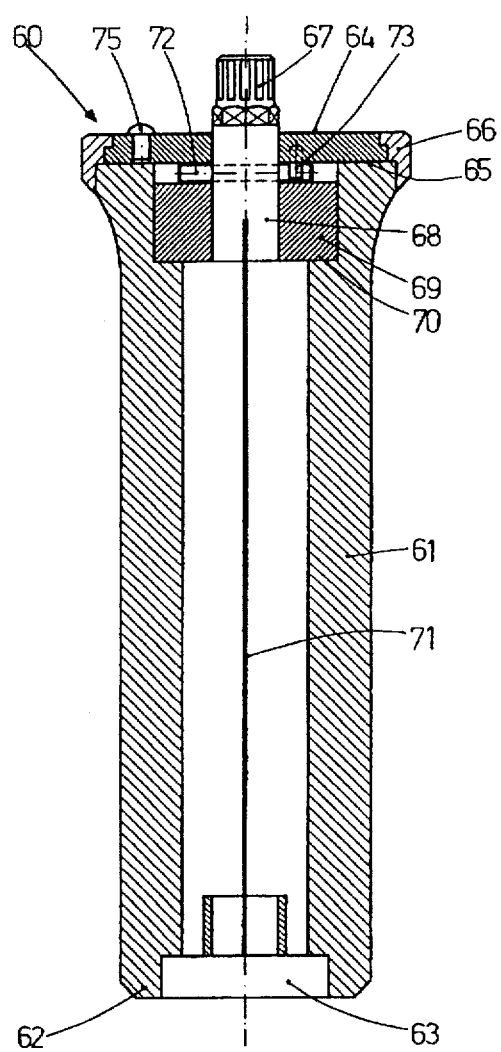
FIG. 4b shows the test device according to FIG. 4a in vertical section.
Figure 4C:
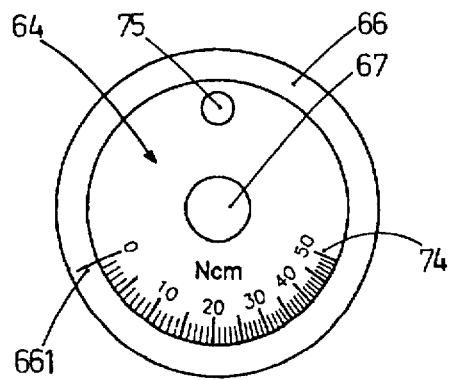
FIG. 4c shows the plan view according to FIG. 4a in arrow direction Y.

The completely assembled torque wrench 1 in this figure comprises a ratchet instrument 10 known per se and the torque indicator 40 pushed on to the latter in the manner of a sleeve. The torque indicator 40 is essentially formed from the sleeve-shaped support 41 and the bending rod 51. The tool head 31 of the downwardly extending screwing-in tool 30, which is known per se is releasably inserted in the ratchet head 11 of the ratchet instrument 10, specifically in a vertical bore 111 intended for the purpose, the tool head 31 having several vertical ratchet grooves 32 on its circumference. The ratchet head 11 is arranged at the very front of the transition region 121 leading to the ratchet handle. A shaft 33 terminating in screw part 34 adjoins the bottom of the tool head 31. At the bottom of the screw part 34 there is a recess in which the complementary head of the screw 2 to be screwed into the implant 3 is received. A guide wrench 4 is attached to the tool head 31. The theoretical axis of rotation 35 extends through the implant 3, the screw 2, the screwing-in tool 30, the ratchet head 11 and the head part of the guide wrench 4. The screwing-in tool 30 is exchangeable; it is chosen so as to suit the contour of the head of the screw 2.

The following applies to the entire further description. If a figure contains reference numerals for the purpose of graphical clarity, while these reference numerals are not explained in the description text immediately pertaining thereto, reference its made to their citation in the descriptions of the preceding figures.

FIG. 1b and 1c

The ratchet instrument 10 principally comprises two assembly units, namely the ratchet handle 12 with the ratchet head 11 attached to the front of the transition region 121, on the one hand, and the bolt rod 15 with the external control knob 25, screw 22 and compression spring 21, on the other hand. Direction arrows 26 pointing in the same direction are provided on the upper and lower sides of the control knob 25. An axially passing bore 13 which opens in the vertical bore 111 provided to receive the tool head 31 in the ratchet head 11 extends through the ratchet handle 12. The bore 13 emerges at the free end of the ratchet handle 12 located opposite the ratchet head 11, the emerging part of the bore 13 being designed as an internal screw thread section 24 complementary to the external screw thread section 28 of the screw 22. In its front region facing the ratchet head 11, the ratchet handle 12 possesses a wedge shape 14 projecting into the bore 13. The wedge shape 14 could be formed by external engraving on the ratchet handle 12. The transition region 121 between the ratchet head 11 and the ratchet handle 12 has a contour that is not rotationally symmetrical.

At its front face the bolt rod 15 has an instrument catch 16 integrally formed with the shaft 27, on the front face of which catch there is a wedge-shaped catch nose 161. A shoulder 162 is provided at the transition between the instrument catch 16 and the thickened shaft 27. The shaft 27 comprises a front section 271 and a longer, rear section 272 between which there is a radially extending groove 273. At the front section 271 there are two flattened sections 19, 19' which are parallel and opposite to each other, extend in the longitudinal direction and reach roughly to the diameter of the instrument catch 16. These flattened sections 19, 19' are continued behind the groove 273 and extend partially over the rear section 272. The rear section 272 terminates in a radially extending shoulder 20, so that the diameter of the bolt rod 15, which is continued from the shoulder 20 as a terminal section 29, is reduced. The compression spring 21 sits on the terminal section 29, followed by the rotatable screw 22 and, finally, the control knob 25. The compression spring 21 abuts the shoulder 20, on the one hand, and the external screw thread section 28 of the screw 22, on the other hand. In the direction of the control knob 25 the screw 22 has a disc-shaped screw head 23 projecting above the ratchet handle 12 and attached to the external screw thread section 28.

When the bolt rod 15 is inserted into the ratchet handle 12 the internal screw thread section 24 of the ratchet handle 12 and the external screw thread section 28 of the screw 22 engage each other. The thickened screw head 23 which can be gripped by the fingers rests against the end of the ratchet handle 12, and the terminal section 29 projects through the external screw thread section 28 and the screw head 23, so that the control knob 25 can also be gripped by the fingers. The bolt rod 15 is inserted in the bore 13 provided in the ratchet handle 12, and the catch nose 161 located at the very front of the instrument catch 16 projects into 20 the vertical bore 111 situated in the ratchet head 11. Penetration of the instrument catch 16 in the direction of the ratchet head 11 is limited in that the shoulder 162 inside the ratchet handle 12 abuts a counter-shoulder. Furthermore, depending on the rotary position of the bolt rod 15 the wedge shape 14 sits on one of the flattened sections 19, 19' on the rear section 272 of the shaft 27. The bolt rod 15 is thus secured against rotation and the catch nose 161 extends in parallel to the axis of rotation 35.

When a screwing-in tool 30 is inserted in the ratchet head 11, the catch nose 161 which is under the tension of the compression spring 21 via the bolt rod 15 engages in a ratchet groove 32 provided on the tool head 31, as a result of which the screwing-in tool 30 is mounted in the vertical bore 111. The catch nose 161 is asymmetrical; in relation to the axis of rotation 35 it possesses a bevelled ratchet flank 17 and a blocking flank 18 aligned approximately at right angles thereto. Corresponding to the direction arrow 26 on the control knob 25 the bolt rod 15 can be fixed in two rotary positions offset by 180° relative to one another in the ratchet handle 12. Accordingly, the catch nose 161 engages in a ratchet groove 32 on the tool head 31 in clockwise or anti-clockwise direction, and the ratchet flank 17 and the blocking flank 18 are aligned in the corresponding direction. The tool head 31 cannot be rotated counter to the blocking flank 18, or the tool head 31 is carried along in the direction of rotation in which the blocking flank 18 points by a pivoting movement of the ratchet instrument 10. When the ratchet instrument 10 is pivoted in the other direction the inclined ratchet flank 17 slides over the ratchet grooves 32 of the fixed screwing-in tool 30. Whenever the catch nose 161 jumps from one ratchet groove 32 into the adjacent groove the bolt rod 15 is minimally displaced counter to the tension of the compression spring 21. In the exemplary embodiment of FIG. 1c —which also corresponds to the orientation of the direction arrow 26—the catch nose 161 engages the tool head 31 in clockwise direction, as a result of which the screwing-in tool 30 is carried along by a pivoting movement in clockwise direction. If the ratchet instrument 10 is guided back in anticlockwise direction the screwing-in tool 30 is not carried along, but the catch nose 161 engages again in a following ratchet groove 32.

The reversal of the carrier function of the ratchet instrument 10 can be adjusted as follows. The bolt rod 15 must be rotated about 180° for this purpose, so that the lower direction arrow 26 comes up and points upwards. For this purpose, the bolt rod 15 must initially be pulled out of the ratchet handle 12 up to the stop by gripping the control knob 25; it is only then that the bolt rod 15 can be rotated by 180°. When the bolt rod 15 is pulled out the flattened section 19 slides on the rear section 272 of the shaft 27 under the wedge shape 14 until the wedge shape 14 arrives in the region of the groove 273. In this extended position the bolt rod 15 can be rotated. However, the rotation about 180° is decisive, with the results that the other flattened section 19' now faces the wedge shape 14. The control knob 25 is now released, whereupon the compression spring 21 pulls the bolt rod 15 back into the ratchet handle 12 and the flattened section 19' is pushed simultaneously on the rear section 272 under the wedge shape 14. The flattened sections 19, 19' on the front section 271 merely have a guiding function and permit the front section 271 to pass the wedge shape 14 on insertion of the bolt rod 15.

The ratchet instrument 10 can be used to transmit a torque onto the screwing-in tool 30, the function of the ratchet instrument 10 being reversible, namely from a right-hand torque to a left-hand torque, e.g. for tightening a screw 2 or for releasing the latter.

In combination with the torque indicator 40 the ratchet instrument 10 results in the ready-to-operate torque wrench 1 according to the invention. The tubular support 41 possesses at its front a widened insertion zone 42 which is complementary, i.e. positively locking, for partial reception of the transition region 121. When the support 41 is pushed onto the ratchet handle 12 the shoulder of the transition region 121 is inserted in the insertion zone 42. As a result of the non-rotationally symmetrical contours of the transition region 121 and the insertion zone 42, the ratchet handle 12 and the support 41 are secured against rotation relative to one another. The support end 43 extends at least to the gripping end 122 as a result of which the screw head 23 comes to bear against the support end 43. When the screw 22 is tightened the insertion zone 42 is pressed onto the shoulder of the transition region 121.

The fixed end of the linearly elastic bending rod 51 is firmly arranged behind the insertion zone 42 on the support 41 at the clamping site 45. A clamping head 44 located in a raised position on the support 41 is preferably provided for fixation of the bending rod 51. The bending rod 51 extends in the horizontal plane parallel to the longitudinal axis 46, extends beyond the control knob 25 and is provided at its free end with a finger member 52. In the vicinity of the support end 43, a web 47 on which a graduation 48 is provided is attached so as to be aligned at right angles to the support 41 and at right angles to the bending rod 51. The web 47 simultaneously has a guiding function for the bending rod 51 deflected during operation. The bending rod 51 is pulled forward from a zero position by a force F acting upon the finger member 52. Depending on the magnitude of the force F the bending rod 51 is bent up to the adequate value on the graduation 48, which is calibrated, e.g. in Ncm. The bending rod 51 should not have any contact with the web 47 in order to avoid measurement errors due to friction.

The ratchet instrument 10 and the torque indicator 40 are assembled as follows: the ratchet instrument 10 is dismantled into the ratchet handle 12 with the ratchet head 11 present thereon, as well as into the bolt rod 15 with the compression spring 21 located thereon, screw 22 and control knob 25. The support 41 together with the bending rod 51 attached thereon is pushed, with the insertion zone 42 at the front, over the ratchet handle 12 until there is positive locking between the insertion zone 42 and the transition region 121. Thereupon, the bolt rod 15 is pushed into the bore 13, one of the flattened sections 19, 19' sliding under the wedge shape 14. Finally, the screw 22 is screwed in such that the screw connection between the external screw thread section 28 and the internal screw thread section 24 is produced. After checking the desired rotary position of the control knob 25 the torque wrench 1 is ready to operate.

FIG. 2a to 3a

Advantageously, two parallel webs 47 are provided which are at a distance from one another and between which the bending rod 51 projects, so that the bending rod 51 can only be moved within the slot 471 formed by the two webs 47. Thus, the direction for the application of the force F on the finger member 52 is predetermined and tilted use of the torque wrench 1 is excluded.

The torque wrench 1 can be dimensioned on the basis of the known formulae, a specific deflection of the bending rod 51 corresponding to an analogous torque M exerted upon the screwing-in tool 30.

FIG. 3b

In a further embodiment of the torque indicator 40, a maximum indicator 49 for marking the maximum deflection of the bending rod 51 and a stop 50 for delimiting its maximum possible deflection are provided on the webs 47. An alloy which has proven particularly suitable for the bending rod 51 is based on Co—Ni—Cr with additions of Be and Ti in the form of a smooth, precision-ground and quenched wire which is hard-drawn by a cold method and which has a diameter of 1.25 mm and a modulus of elasticity within the range from 215 to 230 kN/mm$^2$.

FIG. 4a to 4c

The test device 60 provided for control of the accuracy of the torque wrench 1 with the attached torque indicator has a cylindrical housing 61 which is gripped by one hand on actuation. In the housing floor 62 there is a fixed bottom plate 63, whereas the housing 61 possesses a disc-shaped rotatable lid 64 at the very top. The lid 64 rests slidingly on the upper housing edge 65 and is radially mounted in a fixed sliding ring 66 connected to the housing 61. An instrument head 67 onto which the ratchet instrument 10 can be applied with its ratchet head 11 projects axially through the lid 64. The instrument head 67 possesses a contour that is identical to the tool head 31. The lid 64 and the instrument head 67 can each be rotated relative to one another. The downwardly extending shaft 68 of the instrument head 67 is rotatably mounted in a slide bush 69 which sits firmly in a housing recess 70.

A leaf spring 71 which extends axially through the test device 60 and can be subjected to a torsional load is loosely held, on one side, in the shaft 68 and, on the other side, in the bottom plate 63. A carrier 72—in the present case a firmly seated transverse pin projecting horizontally through the shaft 68—is arranged between the lid 64 and the slide bush 69. A stop element 73 fixed on the underside of the lid 64—in the present case in the form of a vertical pin inserted into the lid 64—projects into the region of the carrier 72. A scale 74 for the measured torques is provided on the very top of the lid 64. Furthermore, an adjustment element 75 is located on top of the lid 64 in order to provide a better hold for the fingers when it is intended to adjust the lid 64. This is necessary for adjustment of the zero position after a previous control procedure. The scale 74 provided on the lid 64 is located in the zero position if the scale value "0" appears at the zero mark 661 provided on the fixed sliding ring 66.

FIGS. 5a to 5d

Figure 5A:
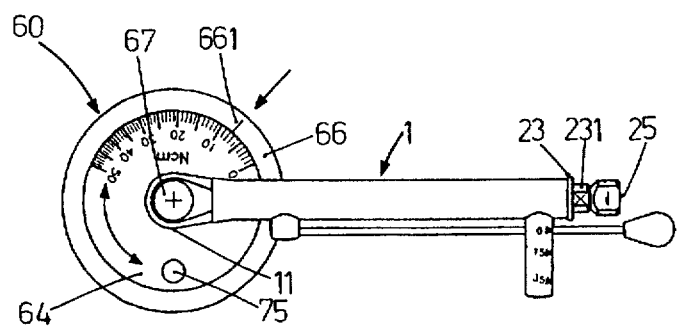
FIG. 5a shows the torque wrench attached to the test device in the starting situation.

In the procedure for controlling the accuracy of a torque wrench 1 by means of the test device 60 the latter functions as follows:

A) Starting situation according to FIG. 5a The test device 60 is either clamped so as to be fixed against rotation or—in the normal case—it is held by one hand on the housing 61. The complete torque wrench 1 to be tested is attached to the instrument head 67 of the test device 60. The scale 74 is still in the position deviating from the zero position from the previous check, i.e. the lid 64 is still displaced and the scale value "0" does thus not appear at the zero mark 661. The leaf spring 71 is relaxed.

Figure 5B:
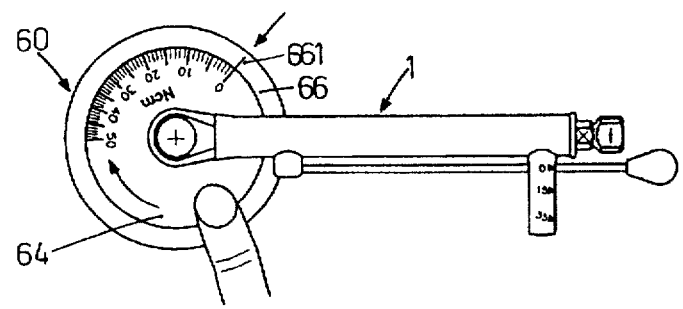
FIG. 5b shows the representation according to FIG. 5a with the test device in the zero position.

B) Zero position according to FIG. 5b

By turning the lid 64 the scale value "0" is brought to coincide with the zero mark 661. Inside the test device 60, the stop element 73 is thereby now brought directly up to the resting carrier 72.

Figure 5C:
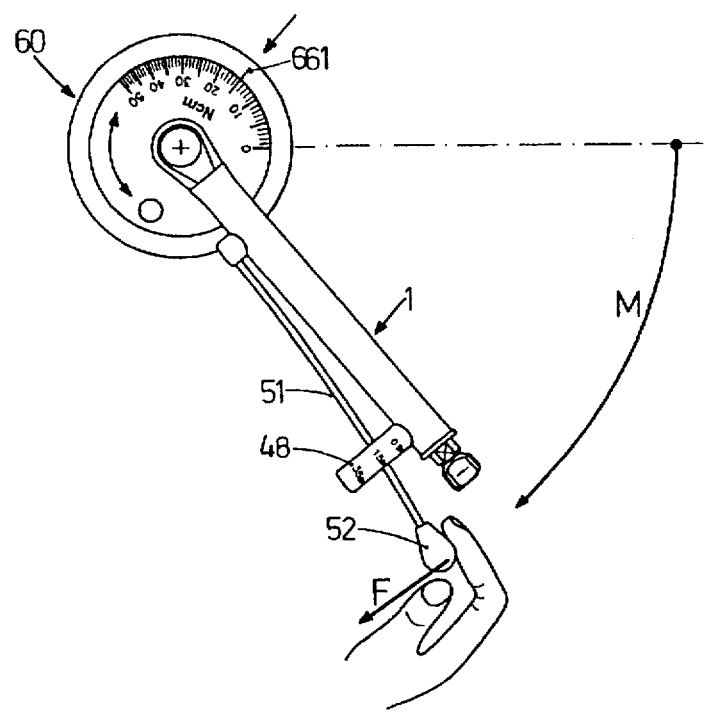
FIG. 5c shows the representation according to FIG. 5a with the deflected torque wrench in the test.

C) Control load according to FIG. 5c

A specific torque M is then applied upon the finger member 52; in the present example this is 15 Ncm. This value must be displayed by the deflected bending rod 51 on the graduation 48. As a result of this, the instrument head 67 is rotated together with the shaft 68, carrier 72 and the leaf spring 71. Inside the test device 60, the stop element 73 is accordingly pushed by the carrier 72 and the lid 64 is adjusted in accordance with a maximum indicator. The test device 60 is dimensioned such that the torque M exerted upon the finger member 52 is displayed on the scale 74 of the test device 60.

Figure 5D:
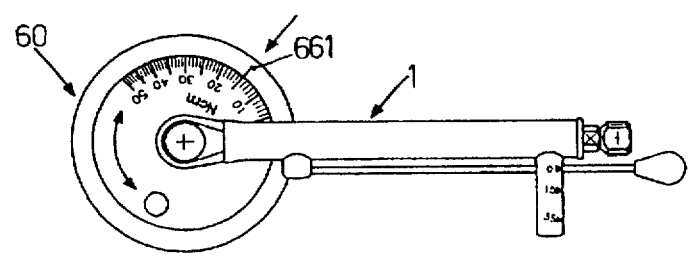
FIG. 5d shows the representation according to FIG. 5a with the retracted torque wrench after the test.

D) After the control load according to FIG. 5d

When the force F applied upon the finger member 52 is successively reduced the torque wrench 1 is pressed by the leaf spring 71 back into the horizontal resting position. The carrier 72 and the stop element 73 thereby move away from each other, the lid 64 remaining in the deflected position, however. For control purposes, the measurement value can thus still be read off the scale 74. The torque wrench 1 tested here functions properly because the value previously displayed on the graduation 48 coincides with the value determined on the scale 74. In the event of deviations of measured values beyond a permissible tolerance the torque wrench 1 must be calibrated again.

Further constructional variations can be implemented for the abovementioned embodiments. The following may be expressly mentioned in addition:

the support 41 can be dispensed with if the bending rod 51 and the webs 47 would be immediately attached to the outside of the ratchet handle 12.

The screw 22 also possesses a polyhedral segment 231 (see FIG. 5a) behind the previous screw head 23 if tightening of the screw 22 with a wrench is desired.

Instead of being combined with the ratchet instrument 10 the torque indicator 40 can also be combined with an equivalent instrument with which a tool to be rotated is guided directly or indirectly.

The leaf spring 71 can be firmly clamped in the shaft 68 and/or in the bottom plate 63.

We claim:

1. A surgical torque wrench, comprising:
   a torque instrument; and
   a torque indicator having:
   an elongated rigid support mountable on the torque instrument,
   a linearly elastic bending rod extending along the support and having one end thereof fixedly secured to the support at a clamping site of the support, and graduation means provided on the support and extending transverse to the support for indicating a torque generated by application of a force to a free end of the bending rod and determined by deflection of the bending rod relative to the graduation means,
   wherein the support is formed as a sleeve having at a front end thereof, adjacent to the clamping site, a non-rotationally symmetrical insertion zone for receiving a transition region of the torque instrument located between a head and a handle of the torque instrument, the support extending to an end of the handle remote from the head, and wherein the wrench further comprises a screw turnable into the remote end of the handle for axially fixing the support.

2. A surgical torque wrench according to claim 1, wherein the support includes a clamping head located in vicinity of the transition region for fixedly securing the one end of the bending rod to the support; wherein the graduation means comprises a projecting web having a graduation and located at a rear end of the support; wherein the bending rod extends, in a non-deflected position thereof, parallel to a longitudinal axis of the torque wrench and is deflected in a plane in which the longitudinal axis of the wrench lies, the bending rod extending beyond the web.

3. A surgical torque wrench, comprising:
   a torque instrument; and
   a torque indicator having:
   an elongated rigid support mountable on the torque instrument,
   a linearly elastic bending rod extending along the support and having one end thereof fixedly secured to the support at a clamping site of the support, and graduation means provided on the support and extending transverse to the support for indicating a torque generated by application of a force to a free end of the bending rod and determined by deflection of the bending rod relative to the graduation means,
   wherein the graduation means comprises two projecting webs extending parallel to each other and defining together a slot, with graduation being provided on each of the two webs; wherein the bending rod has a rear free portion displaceable in the slot; wherein the graduation means includes at least one of a stop provided on the webs and a maximum indicator; and wherein the bending rod is provided with a finger member at the free end thereof.

4. A surgical torque wrench, comprising:
   a torque instrument; and
   a torque indicator having:
   an elongated rigid support mountable on the torque instrument,
   a linearly elastic bending rod extending along the support and having one end thereof fixedly secured to the support at a clamping site of the support, and graduation means provided on the support and extending transverse to the support for indicating a torque generated by application of a force to a free end of the bending rod and determined by deflection of the bending rod relative to the graduation means,
   wherein the bending rod is made of an alloy based on Co—Ni—Cr with additions of Be and Ti and is formed as a smooth, precision and quenched wire by a cold method, and wherein the wire has a diameter of 1.25 mm and a modulus of elasticity within a range of 215–230 KN/mm2.

5. An assembly, comprising a surgical torque wrench comprising:
   a torque instrument; and
   a torque indicator having:
   an elongated rigid support mountable on the torque instrument,
   a linearly elastic bending rod extending along the support and having one end thereof fixedly secured to the support at a clamping site of the support, and graduation means provided on the support and extending transverse to the support for indicating a torque generated by application of a force to a free end of the bending rod and determined by deflection of the bending rod relative to the graduation means,
   wherein the support is formed as a sleeve having at a front end thereof, adjacent to the clamping site, a non-rotationally symmetrical insertion zone for receiving a transition region of the torque instrument located between a head and a handle of the torque instrument, the support extending to an end of the handle remote from the head, and wherein the wrench further comprises a screw turnable into the remote end of the handle for axially fixing the support;
   and a test device for controlling display accuracy of the torque indicator of the surgical torque wrench, comprising:
   a cylindrical housing having a bottom plate;
   a lid rotatably attached to a housing top, the lid serving as a maximum torque indicator;
   a sliding ring provided at the housing top for connecting the lid with the housing;
   a rotatable instrument head for receiving the surgical torque wrench, the instrument head having a downwardly projecting shaft extending through the lid and rotatably supported in a slide bush located in a recess formed at the top end of the housing;
   a leaf spring located between the shaft and the bottom plate; and
   a carrier fixed on the shaft between the lid and the slide bush for displacing a stop element provided on underside of the lid, together with the lid, from a zero position.

6. An assembly according to claim 5, wherein the test device further comprises a scale provided on a lid top and a complementary zero mark provided on the sliding ring, the lid being located in a zero position thereof when a "0" value of the scale coincides with the complementary zero mark.

7. An assembly according to claim 6, wherein the carrier is formed as a pin extending transversely through the shaft, and the stop element is formed as a pin projecting from a lid bottom; wherein the test device further comprises an adjusting element provided on the lid top; and wherein the scale corresponds to a graduation of the torque indicator of the torque wrench.

* * * * *